(12) United States Patent
Tu et al.

(10) Patent No.: US 9,149,458 B1
(45) Date of Patent: Oct. 6, 2015

(54) **METHOD FOR TREATING HYPERTRIGLYCERIDEMIA WITH A *WEDELIA CHINENSIS* EXTRACT**

(71) Applicant: Wyntek Corporation, Taipei (TW)

(72) Inventors: Tseng-Rong Tu, Taitung County (TW); Wen-Mai Hsu, Taoyuan County (TW); Eugene Fan, La Jolla, CA (US)

(73) Assignee: Wyntek Corporation, Taipei (TW)

( * ) Notice: Subject to any disclaimer, the term of this patent is extended or adjusted under 35 U.S.C. 154(b) by 0 days.

(21) Appl. No.: 14/613,032

(22) Filed: Feb. 3, 2015

(51) Int. Cl.
  *A61K 31/366* (2006.01)
  *A61K 31/353* (2006.01)
  *A61K 36/28* (2006.01)

(52) U.S. Cl.
  CPC ............. *A61K 31/366* (2013.01); *A61K 31/353* (2013.01); *A61K 36/28* (2013.01)

(58) Field of Classification Search
  USPC ........................................................ 514/456
  See application file for complete search history.

(56) References Cited

U.S. PATENT DOCUMENTS

| | | | |
|---|---|---|---|
| 7,375,112 | B2 | 5/2008 | Friesen et al. |
| 8,597,701 | B2 | 12/2013 | Hsiao |

OTHER PUBLICATIONS

Abourjaili, et al., "Current concepts in triglyceride metabolism, pathophysiology, and treatment", Metabolism Clinical and Experimental, vol. 59, 2010.
Atar, et al., "Is there any relationship between coronary artery disease and postprandial triglyceride levels?", Anadolu Kardiyol Derg, 2011.
Austin, et al., "Hypertriglyceridemia as a Cardiovascular Risk Factor", American Journal of Cardiology, vol. 81, No. 4A, 1998.
Fossati, et al., "Serum Triglycerides Determined Colorimetrically with an Enzyme That Produces Hydrogen Peroxide", Clinical Chemistry, vol. 28, No. 10, 1982.
Kalia, et al., "Determination of serum triglycerides using lipase, glycerol kinase, glycerol-3-phosphate oxidase and peroxidase co-immobilized onto alkylamine glass beads", Indian Journal of Biochemistry & Biophysics, vol. 41, pp. 326-328, Dec. 2004.
Lin, et al., "Compounds from *Wedelia chinesis* synergistically suppress androgen activity and growth in prostate cancer cells", Carcinogenesis, vol. 28, No. 12, 2007.
Miller, et al., Triglycerides and Cardiovascular Disease: A Scientific Statement From the American Heart Association, American Heart Association Circulation, 2011; 123:2292-2333, Apr. 2011.
Nelson, "Hyperlipidemia as a Risk Factor for Cardiovascular Disease", NIH Public Access Author Manuscript, Prim Care, 2013.
Nomani, et al., "Evaluation of antidiabetic potentiality of methanolic extract of *Wedelia chinesis* whole plant", International Journal of Pharmaceutical and Biomedical Research, vol. 4, No. 4, 2013.
Pearson, et al., "AHA Guidelines for Primary Prevention of Cardiovascular Disease and Stroke: 2002 Update Consensus Panel Guide to Comprehensive Risk Reduction for Adult Patients Without Coronary or Other Atherosclerotic Vascular Diseases", Circulation, Jul. 2002.
Prejic, et al., "Hypertriglyceridemia", Evidence Based Clinical Medicine, JABFM, vol. 19, No. 3, May-Jun. 2006.
Sarwar, et al., "Triglycerides and the Risk of Coronary HJeart Disease 10 158 Incident Cases Among 262 525 Participants in 29 Western Prospective Studies", Circulation, Jan. 2007.
Swartz, "Ultra Performance Liquid Chromatography (UPLC): An Introduction", Separation Science Identified, May 2005.
Yuan, et al., "Hypertriglyceridemia: its etiology, effects and treatment", CMAJ, vol. 176, No. 8, Apr. 2007.

*Primary Examiner* — Kristin Vajda
(74) *Attorney, Agent, or Firm* — Cesari & McKenna, LLP

(57) ABSTRACT

A method for treating hypertriglyceridemia with a composition containing wedelolactone, luteolin, and apigenin. Also provided is a method for reducing the risk of developing hypertriglyceridemia by administering the composition to a subject at risk thereof. The composition can be an extract of *Wedelia chinensis*.

22 Claims, 2 Drawing Sheets

METHOD FOR TREATING HYPERTRIGLYCERIDEMIA WITH A *WEDELIA CHINENSIS* EXTRACT

BACKGROUND

1. Field

This application relates to the treatment of hypertriglyceridemia and reducing the risk of developing this condition.

2. Background Information

A triglyceride is an ester derived from glycerol and three fatty acids. Triglycerides are the main lipid component of dietary fat and fat depots of animals. Triglycerides are transferred via the blood between tissues, e.g., between adipose tissue and liver tissue, by lipoprotein particles. The highest triglyceride concentrations are found in chylomicrons and very low density lipoprotein particles.

The American Heart Association classifies individuals by their fasting serum triglyceride levels as follows: <150 mg/dL, normal; 150 to 199 mg/dL, borderline high; 200 to 499 mg/dL, high; and ≥500 mg/dL, very high. Elevated triglyceride levels, known as hypertriglyceridemia, contribute to the development of atherosclerosis, cardiovascular disease, and acute pancreatitis.

Most often, hypertriglyceridemia is caused by obesity, lipodystrophic disorders, diabetes mellitus, metabolic syndrome, and chronic kidney disease. In some instances, it can be caused by familial genetic disorders.

Typically, life-style modifications are recommended for individuals having borderline high triglyceride levels (150 to 199 mg/dL). Lifestyle modifications encompass changes in diet, exercise, weight reduction, smoking cessation, and limiting alcohol intake. Optimization of nutrition can result in a marked reduction in serum triglycerides by as much as 20% to 50%.

Patients with levels of triglycerides greater than 200 mg/dL are prescribed lipid-lowering drugs. The major pharmacological treatment options for hypertriglyceridemia are HMG-CoA reductase inhibitors (e.g., atorvastatin, fluvastatin, pitavastatin, pravastatin, lovastatin, simvastatin, and rosuvastatin), fibric acid derivatives (e.g., gemfibrozil and fenofibrate), nicotinic acid (niacin), cholesterol absorption inhibitors, bile acid sequestrates (resins), and ω-3-acid ethyl esters.

Current pharmacological treatments for hypertriglyceridemia do not effectively control high triglyceride levels without unfavorable adverse effects. The need exists for efficient treatments for hypertriglyceridemia that have fewer side effects.

SUMMARY

To meet the need discussed above, a method for treating hypertriglyceridemia is disclosed. The method includes the steps of identifying a subject having hypertriglyceridemia and administering to the subject an effective amount of a composition containing wedelolactone, luteolin, and apigenin.

Also disclosed is a method for reducing the risk of developing hypertriglyceridemia. This method includes the steps of identifying a subject at risk of developing hypertriglyceridemia and administering to the subject an effective amount of a composition containing wedelolactone, luteolin, and apigenin.

The details of one or more embodiments of the invention are set forth in the description, in the drawings, and in the examples below. Other features, objects, and advantages of the invention will be apparent from the detailed description of several embodiments and also from the claims. All publications and patent documents cited herein are incorporated by reference in their entirety.

BRIEF DESCRIPTION OF THE DRAWINGS

The invention description below refers to the accompanying drawings, of which.

DETAILED DESCRIPTION

Figure 1A:
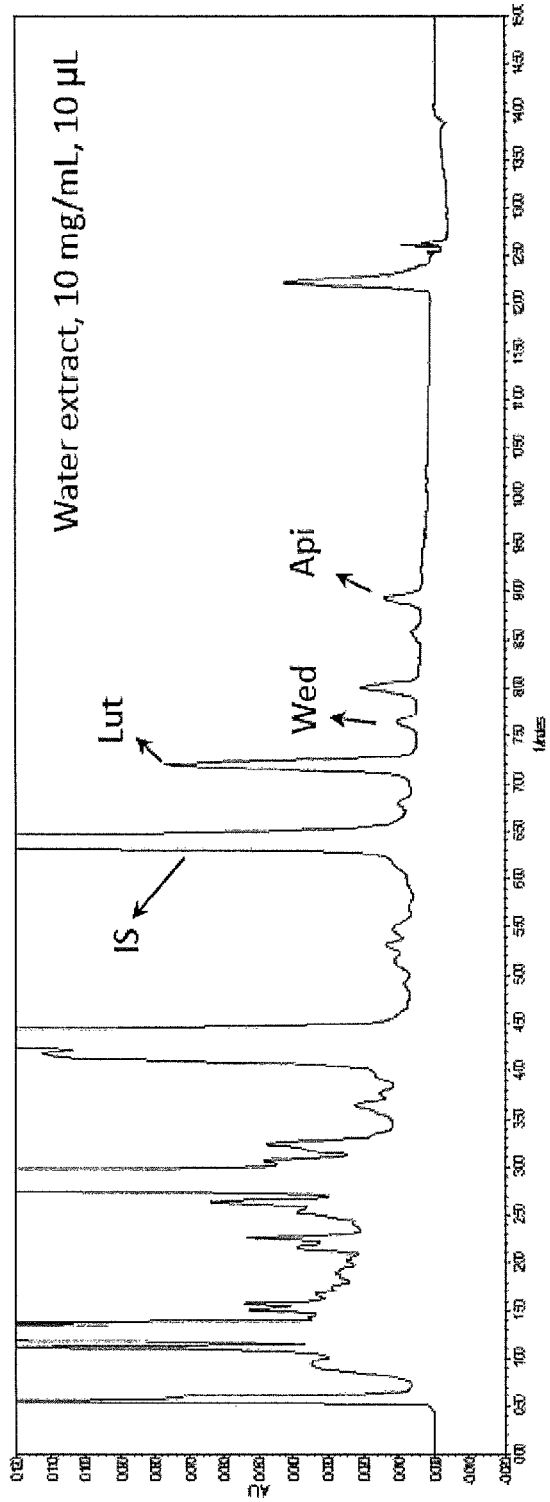
FIG. 1A is a graph depicting an ultrahigh performance liquid chromatography (UPLC) analysis of an acidic aqueous extract of *Wedelia chinensis;*

As mentioned above, a method for treating hypertriglyceridemia is disclosed. The method includes a step of identifying a subject suffering from this condition. The hypertriglyceridemia can be detected by methods known in the art. See, e.g., Fossati et al., Clin. Chem. 28:2077-2080 and Kalia et al., Indian J. Biochem. Biophys. 41:326-328. The subject can have a fasting serum triglyceride level of at least 500 mg/dL or a fasting serum triglyceride level of from 500 mg/dL to 1000 mg/dL. Alternatively, the subject can have a fasting serum triglyceride level greater than 1000 mg/dL.

The hypertriglyceridemia can result from alcoholism, diabetes, obesity, metabolic syndrome, hypothyroidism, nephrotic syndrome, pregnancy, nonalcoholic fatty liver disorder, paraproteinemias, and autoimmune disorders. See e.g., Yuan et al., Canadian Med. Assoc. J. 176: 1113-1120. The hypertriglyceridemia can also result from any combination of these medical conditions.

Additionally, the hypertriglyceridemia can be a result of a drug treatment. The drug can be, e.g., a thiazide diuretic, a beta-adrenergic blocking agent, oral estrogen, tamoxifen, a glucocorticoid, oral isotretinoin, an atypical anti-psychotic, a bile acid binding resin, cyclophosphamide, a psychotropic medication, an immunosuppressant, a protease inhibitor, and an anti-retroviral agent. See, e.g., Yuan et al. and Pejic et al., J. Am. Board Fam. Med. 19:310-316.

In another aspect of the method, the hypertriglyceridemia in the subject can result from a lipoprotein lipase deficiency and an apolipoprotein C-II deficiency. In a particular aspect, the subject has familial hyperlipidemia or familial hypertriglyceridemia.

The method for treating hypertriglyceridemia also requires a step of administering to the subject a composition containing wedelolactone, luteolin, and apigenin. The composition can be an extract from *Wedelia chinensis*. More particularly, the extract from *Wedelia chinensis* can be an acidic aqueous extract. Alternatively, the extract from *Wedelia chinensis* can be an ethanolic extract. Further, the composition can be a mixture of pure wedelolactone, luteolin, and apigenin.

The composition can have a weight ratio between wedelolactone, luteolin, and apigenin of 1:5.5-75:0.05-25. For example, the composition can have a weight ratio between wedelolactone, luteolin, and apigenin of 1:12:1.5.

Additionally, the composition to be administered can contain 0.0001% to 10% of wedelolactone, luteolin, and apigenin by weight of the composition.

A method for reducing the risk of developing hypertriglyceridemia is also disclosed. The method requires first identifying a subject at risk of developing hypertriglyceridemia.

The risk of developing hyperlipidemia can be related to another medical condition. For example, the subject at risk for developing hypertriglyceridemia can be suffering from alcoholism, diabetes, obesity, metabolic syndrome, hypothyroidism, or nephrotic syndrome. The subject at risk for developing hypertriglyceridemia can also suffer from any combination of these medical conditions.

In a particular aspect of the method, the subject at risk for developing hypertriglyceridemia has a family history of coronary heart disease.

A subject can also be at risk for developing hypertriglyceridemia as a result of lifestyle choices. For example, the subject can have a diet with a positive energy-intake balance and a high fat or high glycemic index. Alternatively, the subject can be under stress, can be physically inactive, and can be a smoker.

Additionally, the subject at risk for developing hypertriglyceridemia can have normal to mildly elevated serum triglyceride levels. For example, the subject having one or more of the risk factors described above can have a serum triglyceride level of <150 mg/dL. Alternatively, the subject can have a serum triglyceride level of 150 mg/dL to 199 mg/dL.

The subject at risk for developing hypertriglyceridemia can be identified by a physician or other medical professional by examining the subject with regard to the medical conditions, family history, lifestyle choices, and serum triglyceride levels discussed above.

The method for reducing the risk of developing hypertriglyceridemia also requires a step of administering to the subject a composition containing wedelolactone, luteolin, and apigenin. The composition can be an extract from *Wedelia chinensis*. More particularly, the extract from *Wedelia chinensis* can be an acidic aqueous extract. Alternatively, the extract from *Wedelia chinensis* can be an ethanolic extract. Further, the composition can be a mixture of pure wedelolactone, luteolin, and apigenin.

As mentioned above, the composition can have a weight ratio between wedelolactone, luteolin, and apigenin of 1:5.5-75:0.05-25, e.g., 1:12:1.5. The composition to be administered can contain 0.0001% to 10% of wedelolactone, luteolin, and apigenin by weight of the composition.

Without further elaboration, it is believed that one skilled in the art can, based on the disclosure herein, utilize the present invention to its fullest extent. The following specific examples are, therefore, to be construed as merely descriptive, and not limitative of the remainder of the disclosure in any way whatsoever.

EXAMPLES

Example 1

Preparation of an Acidic Aqueous Extract of *W. Chinensis*

Whole *W. chinensis* plants were dried and crushed into pieces having a size less than 0.2 cm. 250 mL of food grade acetic acid (99.8%) and 750 mL of reverse osmosis water ("RO $H_2O$") were added to 100 g of crushed *W. chinensis*. The mixture thus formed was boiled for 90 min. and then cooled to room temperature. The boiled mixture was filtered to remove insoluble residue. The filtrate was concentrated to a volume of ~35 mL in a rotary evaporator. The concentrate was diluted to a volume of 1 L with $H_2O$ and evaporated again. The dilution and evaporation steps were repeated until the pH of the diluted material was above 4.0. The concentrated *W. chinensis* acidic aqueous extract thus obtained was mixed with an equal weight of microcrystalline cellulose. The mixture was stirred for 10 min. and then freeze-dried.

An analysis of the *W. chinensis* acidic aqueous extract was performed by ultrahigh performance liquid chromatography (UPLC). See Swarz, LC-GC North America Supplement 23:8-14. The results, shown in FIG. 1A, indicated that the three major active components of the acidic aqueous extract, namely, wedelolactone, luteolin, and apigenin, were present at a weight ratio of approximately 1:14:2.

The biological activity of the *W. chinensis* acidic aqueous extract was tested using an in vitro cell culture-based assay essentially as described in Lin et al., Carcinogenesis 28:2521-2529 ("Lin"), the content of which is hereby incorporated by reference in its entirety.

Figures 2A, 2B:
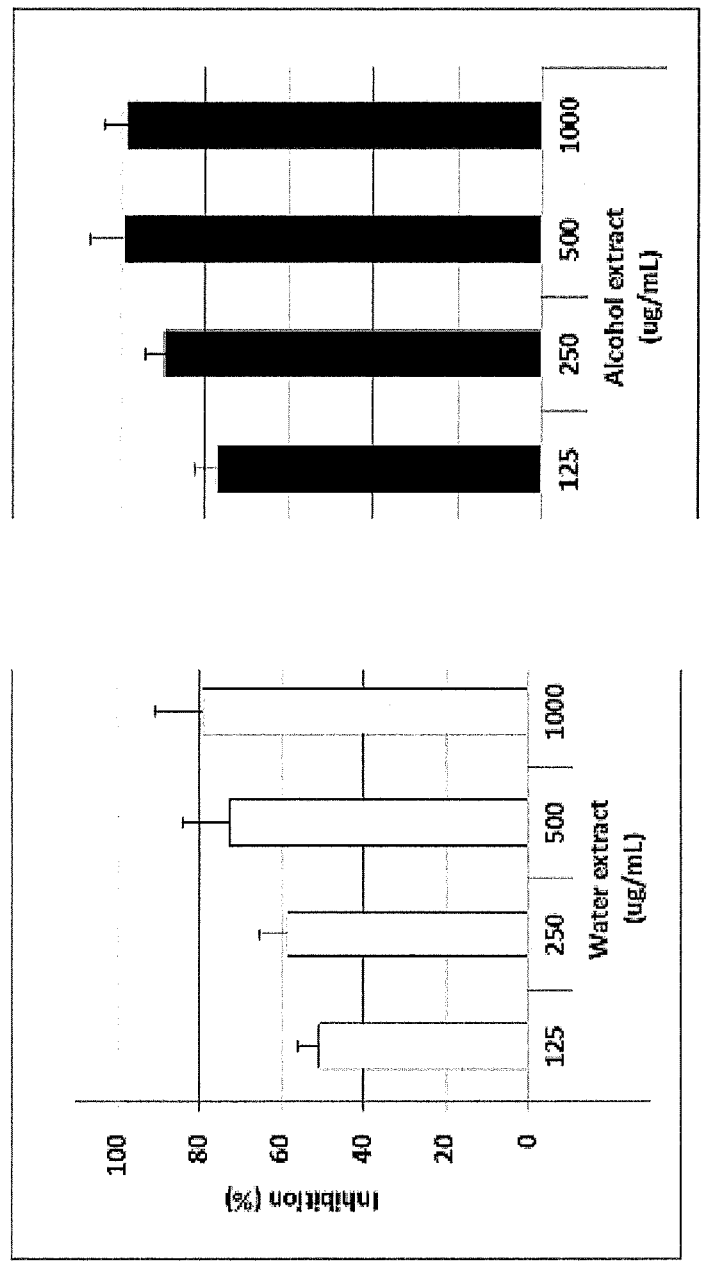
FIG. 2A is a bar graph depicting a bioassay for androgen receptor antagonist activity of an acidic aqueous extract of *Wedelia chinensis.
* and FIG. 2B is a bar graph depicting a bioassay for androgen receptor antagonist activity of an ethanolic extract of *Wedelia chinensis.*

In brief, cultured prostate cancer cells bearing a prostate-specific antigen promoter-luciferase (PSA-LUC) reporter construct was exposed to dihydroxytestosterone (DHA) in the absence (control) or presence of the *W. chinensis* acidic aqueous extract. Luciferase enzyme activity was measured and expressed as percent inhibition as compared to control. The results are shown in FIG. 2A. The *W. chinensis* acidic aqueous extract suppressed as much as 80% of control luciferase activity, demonstrating that the extract can block androgen-induced gene expression.

Example 2

Preparation of an Ethanolic Extract of *W. chinensis*

An ethanolic extract of *W. chinensis* was prepared essentially as described in Lin. UPLC analysis of the ethanolic extract was performed as described above in Example 1. Biological activity was evaluated also as described above.

Figure 1B:
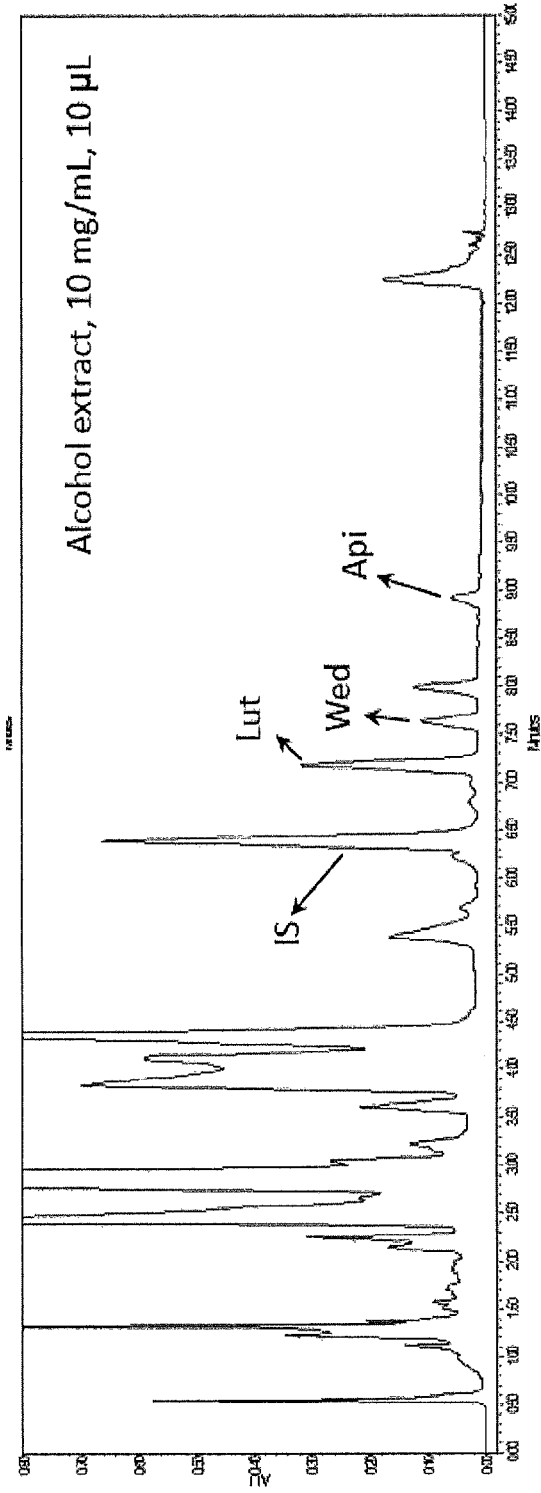
FIG. 1B is a graph depicting a UPLC analysis of an ethanolic extract of *Wedelia chinensis;*

UPLC data (FIG. 1B) and biological activity data (FIG. 2B) indicated that the ethanolic extract had a composition and activity similar to that of the *W. chinensis* acidic aqueous extract.

Example 3

Short Term Treatment of Hypertriglyceridemia with a *W. chinensis* Extract

Five subjects were administered orally with 6 g of the *W. chinensis* acidic aqueous extract described above in Example 1 once daily for 3 months. Serum triglyceride levels in the subjects were measured at the start of treatment and at one-month intervals. The results are shown in Table 1 below.

TABLE 1

| | Lowering of serum triglycerides with a *W. chinensis* extract | | | |
|---|---|---|---|---|
| Subject | day 0 | day 30 | day 60 | day 90 |
| 1 | 159[a] | 129 | 124 | 92 |
| 2 | 175 | 171 | 132 | 66 |
| 3 | 149 | 222 | 188 | 135 |
| 4 | 266 | 159 | 210 | 167 |
| 5 | 172 | 233 | 182 | 152 |

[a]values represent serum triglyceride level expressed as mg/dL

The results indicated that treatment with the *W. chinensis* acidic aqueous extract was successful in lowering serum triglyceride levels in all of the subjects.

Example 4

Long Term Treatment of Hypertriglyceridemia with a *W. chinensis* Extract

A subject having a high blood triglyceride level was administered orally with 6 g per day of the *W. chinensis* acidic aqueous extract described above in Example 1 for a period of 3 months. Subsequently, the dose was reduced to 4 g per day and treatment continued for up to 300 days. Serum triglyceride levels were measured at regular intervals. The results are shown in Table 2 below.

TABLE 2

Long term treatment of hypertriglyceridemia with a *W. chinensis* extract

| Days after start of treatment | serum triglycerides[a] |
|---|---|
| 0 | 268 |
| 120 | 188 |
| 180 | 162 |
| 220 | 109 |
| 260 | 110 |
| 290 | 96 |

[a]serum triglyceride values are expressed as mg/dL

The results indicated that long term treatment with the *W. chinensis* acidic aqueous extract was successful in lowering the serum triglyceride level in a hypertriglyceridemic subject.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, a person skilled in the art can easily ascertain the essential characteristics of the present invention, and without departing from the spirit and scope thereof, can make various changes and modifications of the present invention to adapt it to various usages and conditions. Thus, other embodiments are also within the claims.

The invention claimed is:

1. A method for treating hypertriglyceridemia, the method comprising identifying a subject having hypertriglyceridemia and administering to the subject an effective amount of a composition containing wedelolactone, luteolin, and apigenin.

2. The method of claim 1, wherein the hypertriglyceridemia results from alcoholism, diabetes, obesity, metabolic syndrome, hypothyroidism, nephrotic syndrome, or a combination thereof.

3. The method of claim 1, wherein the hypertriglyceridemia results from a drug treatment.

4. The method of claim 3, wherein the drug is selected from the group consisting of a thiazide diuretic, a beta-adrenergic blocking agent, oral estrogen, tamoxifen, a glucocorticoid, oral isotretinoin, and an anti-retroviral agent.

5. The method of claim 1, wherein the subject has a lipoprotein lipase deficiency or an apolipoprotein C-II deficiency.

6. The method of claim 1, wherein the subject has familial hyperlipidemia or familial hypertriglyceridemia.

7. The method of claim 1, wherein the composition is an acidic aqueous extract or an ethanolic extract of *Wedelia chinensis*.

8. The method of claim 2, wherein the composition is an acidic aqueous extract or an ethanolic extract of *Wedelia chinensis*.

9. The method of claim 3, wherein the composition is an acidic aqueous extract or an ethanolic extract of *Wedelia chinensis*.

10. The method of claim 4, wherein the composition is an acidic aqueous extract or an ethanolic extract of *Wedelia chinensis*.

11. The method of claim 5, wherein the composition is an acidic aqueous extract or an ethanolic extract of *Wedelia chinensis*.

12. The method of claim 6, wherein the composition is an acidic aqueous extract or an ethanolic extract of *Wedelia chinensis*.

13. A method for reducing the risk of developing hypertriglyceridemia, the method comprising identifying a subject at risk of developing hypertriglyceridemia and administering to the subject an effective amount of a composition containing wedelolactone, luteolin, and apigenin.

14. The method of claim 13, wherein the subject suffers from alcoholism, diabetes, obesity, metabolic syndrome, hypothyroidism, nephrotic syndrome, or a combination thereof.

15. The method of claim 13, wherein the subject has a diet with a positive energy-intake balance and a high fat or high glycemic index.

16. The method of claim 13, wherein the subject suffers from stress, is physically inactive, or smokes.

17. The method of claim 13, wherein the subject has a family history of coronary heart disease.

18. The method of claim 13, wherein the composition is an acidic aqueous extract or an ethanolic extract of *Wedelia chinensis*.

19. The method of claim 14, wherein the composition is an acidic aqueous extract or an ethanolic extract of *Wedelia chinensis*.

20. The method of claim 15, wherein the composition is an acidic aqueous extract or an ethanolic extract of *Wedelia chinensis*.

21. The method of claim 16, wherein the composition is an acidic aqueous extract or an ethanolic extract of *Wedelia chinensis*.

22. The method of claim 17, wherein the composition is an acidic aqueous extract or an ethanolic extract of *Wedelia chinensis*.

* * * * *